US012109040B2

(12) United States Patent
Myers

(10) Patent No.: US 12,109,040 B2
(45) Date of Patent: **\*Oct. 8, 2024**

(54) SYSTEM AND METHOD FOR NONINVASIVELY MEASURING BLOOD ALCOHOL CONCENTRATION USING LIGHT

(71) Applicant: Vivonics, Inc., Bedford, MA (US)

(72) Inventor: Ryan Myers, North Andover, MA (US)

(73) Assignee: Vivonics, Inc., Bedford, MA (US)

( * ) Notice: Subject to any disclaimer, the term of this patent is extended or adjusted under 35 U.S.C. 154(b) by 231 days.

This patent is subject to a terminal disclaimer.

(21) Appl. No.: 17/326,713

(22) Filed: May 21, 2021

(65) Prior Publication Data

US 2021/0275092 A1 Sep. 9, 2021

Related U.S. Application Data

(63) Continuation of application No. 16/845,547, filed on Apr. 10, 2020, now Pat. No. 11,013,460.

(Continued)

(51) Int. Cl.
*A61B 5/00* (2006.01)
*A61B 5/024* (2006.01)
*A61B 5/145* (2006.01)

(52) U.S. Cl.
CPC .......... *A61B 5/4845* (2013.01); *A61B 5/0086* (2013.01); *A61B 5/02416* (2013.01); *A61B 5/145* (2013.01)

(58) Field of Classification Search
CPC . A61B 5/4845; A61B 5/0086; A61B 5/02416; A61B 5/145; A61B 5/1495;

(Continued)

(56) References Cited

U.S. PATENT DOCUMENTS

2006/0264718 A1 11/2006 Ruchti et al.
2007/0239992 A1* 10/2007 White .................. B60K 28/063
713/186

(Continued)

FOREIGN PATENT DOCUMENTS

JP 2000230900 A 8/2000
WO 2016178986 A1 11/2016

OTHER PUBLICATIONS

Akl et al., Quantifying Tissue Mechanical Properties Using Photoplethysmography. Biomedical Optics Express, vol. 5 (7). Jun. 19, 2014. DOI:10.1364/BOE.5.002362; fifth and sixth pages, figures 1-2.

(Continued)

*Primary Examiner* — Eric F Winakur
*Assistant Examiner* — Abid A Mustansir
(74) *Attorney, Agent, or Firm* — Iandiorio Teska & Coleman, LLP

(57) ABSTRACT

A system for noninvasively measuring blood alcohol concentration using light includes one or more emitters each configured to emit light in the near infrared or infrared light spectrum at one or more wavelengths that respond to varied chromophore concentrations of ethanol and water in blood of a human subject. One or more detectors is configured to detect light emitted at the one or more wavelengths and output a representation of a photoplethysmography (PPG) waveform for one or more of the one or more wavelengths. A processing subsystem is coupled to the one or more emitters and the one or more detectors. The processing subsystem is configured to determine a measure of an amplitude of the representation of the PPG waveform for each of the one or more wavelengths and determine the blood alcohol concentration by referencing the measured amplitude for each of the one or more wavelengths to a molar absorptivity plot which indicates a measure of the (Continued)

absorption or scattering at alcohol and water solutions ranging between a solution of 100% alcohol and a solution of 100% water.

27 Claims, 7 Drawing Sheets

Related U.S. Application Data

(60) Provisional application No. 62/832,399, filed on Apr. 11, 2019.
(58) Field of Classification Search
CPC ..... A61B 5/681; A61B 5/6828; A61B 5/6829; A61B 5/0075; A61B 5/1455
See application file for complete search history.

(56) References Cited

U.S. PATENT DOCUMENTS

2013/0334419 A1   12/2013  Kluczynski et al.
2018/0214088 A1*  8/2018  Newberry ............ A61B 5/6817

OTHER PUBLICATIONS

Bogen, Emil, "The Diagnosis of Drunkenness—A Quantitative Study of Acute Alcoholic Intoxication", California and Western Medicine, vol. XXVI, No. 6, Apr. 25-28, 1927, 6 pages.
Cech et al., Introduction of a Solid State, Non-Invasive Human Touch Based Alcohol Sensor, Jun. 8, 2015 [online], [retrieved on Jun. 5, 2020], Retrieved from the Internet <URL: https://www-esv.nhtsa.dot.gov/Proceedings/24/files/24ESV-000380.PDF>.
Connor et al., "The Contribution of Alcohol to Serious Car Crash Injuries", Epidemiology, vol. 15, No. 3, May 2004, pp. 337-344.
CCRI.edu. Beer's Law calculations. Jan. 27, 2018, [online], [retrieved on Jun. 5, 2020], Retrieved from the Internet <URL: https://www.ccri.edu/chemistry/courses/chem_1100/wirkkala/reference/Beers_Law_Calculations.pdf>.
German et al., "The Health Benefits of Wine", Annu. Rev. Nutr., 2000, pp. 561-593.
Hurst et al., "The Grand Rapids DIP Revisited", Accid. Anal. and Prev., 26, No. 5, 1994, pp. 647-654.
Liu et al., "Non-Invasive Measurement Study of Human Blood Alcohol Concentration Based on NIR Dynamic Spectrum", IEEE, 2011, 4 pages.
Mariakakis et al., Drunk User Interfaces: Determining Blood Alcohol Level Though Everyday Smartphone Tasks, Apr. 21-26, 2018. Association for Computing Machinery. DOI: 10.1145/3173574.3173808. [online], [retrieved on Jun. 5, 2020], Retrieved from the Internet <URL: https://atm15.github.io/pdfs/dui.pdf>.
Ridder et al., "Noninvasive Alcohol Testing Using Diffuse Reflectance Near-Infrared Spectroscopy", Applied Spectroscopy, vol. 59, No. 2, 2005., pp. 181-189.
Rimm et al., "Review of Moderate Alcohol Consumption and Reduced Risk of Coronary Heart Disease: Is the Effect Due to Beer, Wine, or Spirits?", BMJ 1996, 312 doi: https://doi-org.ezproxy.neu.edu/10.1136/bmj.312.7033.731, 18 pages.
Standridge et al., "Alcohol Consumption: An Overview of Benefits and Risks", Southern Medical Association, 2004, pp. 664-672.
Thakker, Kerstin Damstrom, "An Overview of Health Risks and Benefits of Alcohol Consumption", Alcoholism: Clinical and Experimental Research. vol. 22, No. 7, October Supplement 1998, pp. 285S-298S.
Thun et al., "Alcohol Consumption and Mortality Among Middle-Aged and Elderly U.S. Adults", The New England Journal of Medicine, vol. 337, No. 24, Dec. 11, 1997, pp. 1705-1714.
Louwerens et al., "The Relationship Between Drivers' Blood Alcohol Concentration (BAC) and Actual Driving Performance During High Speed Travel", Alcohol Drugs andTraffic Safety T86 (1987), pp. 183-186.
Reynolds et al., "Alcohol Consumption and Risk of Stroke. A Meta-analysis", JAMA, vol. 289, No. 5, Feb. 5, 2003 pp. 579-588.
Fuchs et al., The New England Journal of Medicine, "The Authors Reply", Oct. 19, 1995, vol. 333, No. 16, p. 1082 (nine (9) pages).
Written Opinion of International Application No. PCT/US2020/027660 date of mailing Jun. 19, 2020, twelve (12) pages.
Topiwala et al., "Moderate Alcohol Consumption as Risk Factor for Adverse Brain Outcomes and Cognitive Decline: Longitudinal Cohort Study", BMJ, 2017, 357, 2353, Jun. 6, 2017, 20 pages.
Borkenstein-RF, "The Role of the Drinking Driver in Traffic Accidents (The Grand Rapids Study)", 1974, 11 (Suppl): one (1) page. https://www.safetylit.org/citations/index.php?fuseaction=citations.viewdetails&citationlds||=citjournalarticle_44212_1.

\* cited by examiner

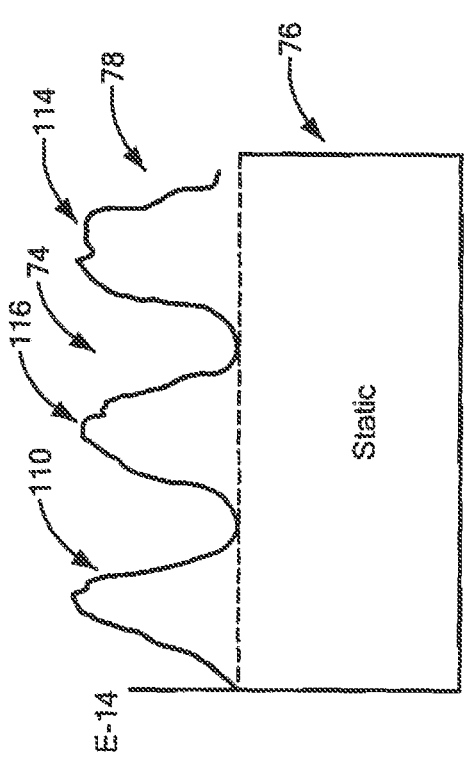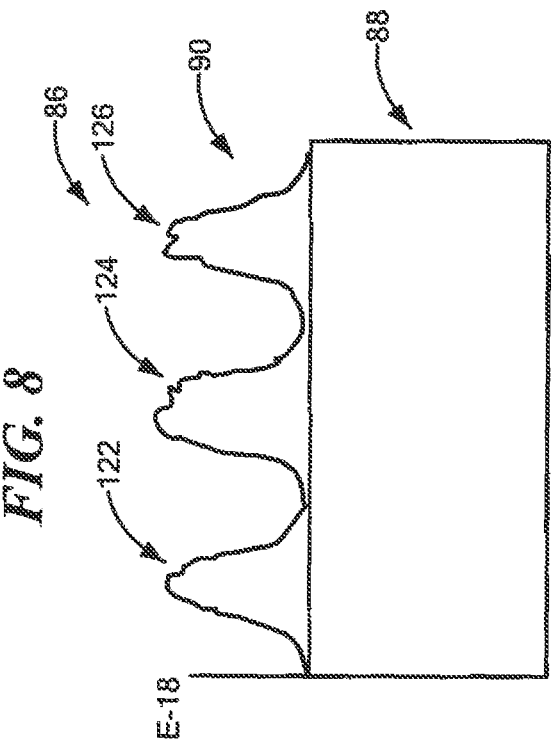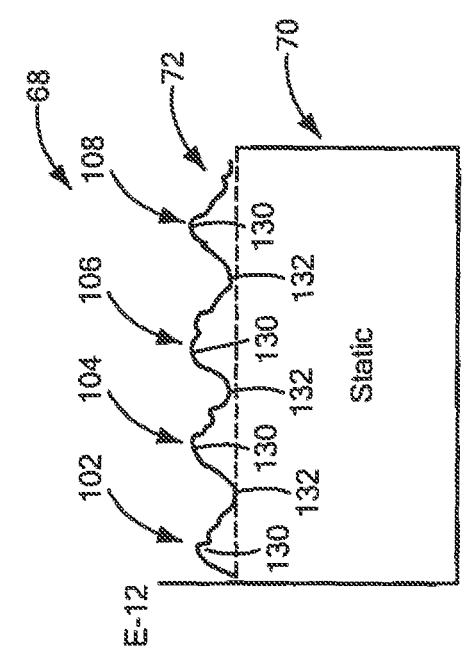

SYSTEM AND METHOD FOR NONINVASIVELY MEASURING BLOOD ALCOHOL CONCENTRATION USING LIGHT

RELATED APPLICATIONS

This application is a continuation of U.S. patent application Ser. No. 16/845,547 filed Apr. 10, 2020 and claims benefit of and priority to U.S. Provisional Application Ser. No. 62/832,399 filed Apr. 11, 2019 under 35 U.S.C. §§ 119, 120, 363, 365, and 37 C.F.R. § 1.55 and § 1.78, which is incorporated herein by this reference.

FIELD OF THE INVENTION

This invention relates to system and method for noninvasively measuring blood alcohol concentration using light.

BACKGROUND OF THE INVENTION

There has been significant research concerning the benefits and detriments of consuming alcoholic beverages. Blood alcohol concentration (BAC) has long been linked to a reduction in driver safety and competency leading to a higher frequency of automobile accidents. See Connor et al., *The Contribution of Alcohol to Series Car Crash Injuries*, Epidemiology, Vol. 15, Number 3, May 2004, incorporated by reference herein. Studies have shown that the slightest amount of alcohol in a driver's system (e.g., about 0.01%) can significantly increase the severity of automobile accidents. See Louwerens, et al., *The Relationship Between Drivers' Blood Alcohol Concentration (BAC) and Actual Driving Performance During High Speed Travel*, Dept. of Clinical Psychiatry, State University Hospital of Groningen, the Netherlands, Elsevier Science Publishers B.V. (1987).

Alcohol consumption and BAC may also have a noticeable physiological effect on the human body. One well known medical condition which may be caused by alcohol abuse is cirrhosis of the liver where the death rate correlates with the volume of daily alcohol consumption. It is also well known that excessive alcohol consumption may also result in cognitive decline. Excessive alcohol consumption may also increase the death rate associated with vehicle accidents which result from impaired decision making and coordination. Excessive alcohol consumption may also cause cancer of the mouth, esophagus, pharynx, larynx, liver, and colorectal region. See Fuchs et al. *The Authors Reply*, Oct. 19, 1995, Vol. 333, No. 16, incorporated by reference herein.

The studies discussed above have also found benefits of consuming alcoholic beverages in moderation. One benefit found was a reduction in the death rate of major cardiovascular conditions, possibly due to a reduction in blood pressure brought on by alcohol consumption. Studies have also shown a few drinks of an alcohol beverage per day may be beneficial but becomes increasingly detrimental as more drinks are consumed.

Similarly, researchers have found that high alcohol consumption (e.g., about 60 grams of alcohol per day) may increase the risk of stroke and reducing alcohol consumption (e.g., about 12 grams per day) may reduce the risk of stroke. See Reynolds et al., *Alcohol Consumption and Risk of Stroke. A Meta-Analysis*, Journal of the American Medical Association, Feb. 5, 2003, Vol. 289, No. 5, incorporated by reference herein. Many other diseases and conditions follow may follow this trend.

As is well known, responsible use of alcohol consumption can easily turn into abuse. In response, communities, law enforcement agencies, and researchers have a vested interest in the ability to monitor BAC to determine the state of inebriation and to understand the side effects and consequences of alcohol consumption. As physiological monitoring devices become commonplace for individual users, e.g., wearable smart devices, such as the Fitbit®, the Apple® watch, and the like, this trend will likely carry to individuals desiring to monitor their own BAC for social, safety, and rehabilitation purposes.

For nearly a century, since the estimation of blood alcohol content through breath analysis was first discovered, there has been a need for a convenient and accurate way to measure BAC. Conventional systems and methods which use near infrared spectroscopy to evaluate BAC are typically large, bulky, cumbersome systems typically only available as table-top systems and use broad near-infrared spectrum, e.g., about 1250 nm to about 2500 nm. Driven by a desire to reduce the impact driving fatalities related to alcohol intoxication, there has been significant strides in creating various conventional technologies to measure BAC of drivers.

However, to date, there has been little focus or effort on providing a wearable system and method to continuously and noninvasively monitor BAC in an accurate, precise, and discreet manner. This is especially true in a clinical setting where the full impact of short term and long term alcohol consumption and use on physiological, psychological and social wellness is understood only at a high level.

Thus, there is a need for a small, compact system and method for noninvasively and accurately measuring BAC that can be configured as a wearable device on a user to allow clinicians to fully understand the impact of short term and long-term alcohol consumption and use on overall health and for individuals to accurately and immediately monitor their own BAC.

SUMMARY OF THE INVENTION

In one aspect, a system for noninvasively measuring blood alcohol concentration using light is featured. The system includes one or more emitters each configured to emit light in the near infrared or infrared light spectrum at one or more wavelengths that respond to varied chromophore concentrations of ethanol and water in blood of a human subject. One or more detectors is configured to detect light emitted at the one or more wavelengths and output a representation of a photoplethysmography (PPG) waveform for one or more of the one or more wavelengths. A processing subsystem coupled to the one or more emitters and the one or more detectors is configured to determine a measure of an amplitude of the representation of the PPG waveform for each of the one or more wavelengths and determine the blood alcohol concentration by referencing the measured amplitude for each of the one or more wavelengths to a molar absorptivity plot which indicates a measure of the absorption or scattering at alcohol and water solutions ranging between a solution of 100% alcohol and a solution of 100% water.

In one embodiment, the processing subsystem may be further configured to average the determined blood alcohol concentration at each of the one or more wavelengths to enhance the accuracy of the measured blood alcohol concentration. The light emitted by the one or more emitters at the one or more wavelengths may be determined by one or more of: an absorptivity or scattered reflectance light spectrum of water, an absorptivity or scattered reflectance light spectrum of alcohol, and/or the molar alcohol absorptivity plot. The one or more detectors may be configured to detect light emitted at one or more wavelengths determined by the one or more of: the absorptivity or scattered reflectance light spectrum of water, the absorptivity or scattered reflectance light spectrum of alcohol, and/or the molar alcohol absorptivity plot. The processing subsystem may be configured to rapidly and sequentially turn on and turn off one or more of the one or more emitters emitting light at the one or more wavelengths. The processing subsystem may be configured to turn on one of more of the one or more emitters to continuously emit the light at the one or more wavelengths. The one or more detectors may be configured to provide the representation of the PPG waveform for each of the one or more wavelengths as an analog representation. The one or more detectors may be configured to provide the representation of the PPG waveform for each of the one or more wavelengths as a digital representation. The processing subsystem may be is configured to determine the measure of the amplitude of the representation of the PPG waveform for each of the one or more wavelengths by one or more of: determining a difference between a maximum PPG value and a minimum PPG value from a dynamic portion of the PPG waveform, determining a route mean square (RMS) value from the dynamic portion of the PPG waveform, determining a maximum PPG peak value from the dynamic portion of the PPG waveform, determining a minimum PPG peak value from the dynamic portion of the PPG waveform, and/or determining a root sum of squares (RSS) from the dynamic portion of the PPG waveform. The system may be configured as a wearable device on the human subject. The one or more detectors, the one or more of emitters, the processing subsystem, a memory, and a power supply each may have a small compact size and may be enclosed in a wearable housing. The emitted light provided by the one or emitters may be transmitted through tissue of the human subject. The one or more detectors may be configured to detect the transmitted light at the one or more wavelengths and output the representation of a photoplethysmography (PPG) waveform for one or more of the one or more wavelengths. At least one of the one or more emitters may be located on one side of an area of the human subject and at least one of the one or more detectors may be located on an opposite side of the area. The emitted light provided by the one or emitters may be scattered in tissue of the human subject. The one or more detectors may be configured to detect reflected scattered light at the one or more wavelengths and output the representation of a photoplethysmography (PPG) waveform for one or more of the one or more wavelengths. At least one of the one of the one or more emitters may be located on a same side of an area of the human subject as at least one of the one or more detectors.

In another aspect, a method for noninvasively measuring blood alcohol concentration using light is featured. The method includes emitting light in the near-infrared or infrared spectrum at one or more wavelengths that respond to varied chromophore concentrations of ethanol and water in blood of a human subject. The method includes detecting light emitted at the one or more wavelengths. The method includes outputting a representation of a photoplethysmography (PPG) waveform for one or more of the one or more wavelengths. The method includes determining a measure of an amplitude of the representation of the PPG waveform for each of the one or more wavelengths, and determining the alcohol concentration by referencing the measured amplitude for each of the one or more wavelengths to a molar absorptivity plot which indicates a measure of the absorption or scattering at alcohol and water solutions ranging between a solution of 100% alcohol and a solution of 100% water.

In one embodiment, the method may include averaging the determined blood alcohol concentration at each of the one or more wavelengths to enhance accuracy of the measured blood alcohol concentration. The light emitted at the one or more wavelengths may be determined by one or more of: an absorptivity or scattered reflectance light spectrum of water, an absorptivity or scattered reflectance light spectrum of alcohol, and/or the molar alcohol absorptivity plot. Detecting the light may include detecting the light emitted at the one or more wavelengths determined by one or more of: the absorptivity or scattered reflectance light spectrum of water, the absorptivity or scattered reflectance light spectrum of alcohol, and/or the molar alcohol absorptivity plot. The method may include rapidly and sequentially emitting the light in the near-infrared or infrared light spectrum at the one or more wavelengths. The method may include continuously emitting the light in the near-infrared or infrared light spectrum at the one or more wavelengths. The representation of the PPG waveform for each of the one or more wavelengths may be an analog representation. The representation of the PPG waveform for each of the one or more waveforms may be a digital representation. Determining the measure of the amplitude of the representation of the PPG waveform may include one or more of: determining a difference between a maximum PPG value and minimum PPG value from a dynamic portion of the representation of PPG waveform, determining a route mean square (RMS) value from the dynamic portion of the PPG waveform, determining a maximum PPG peak value from the dynamic portion of the PPG waveform, determining a minimum PPG peak value from the dynamic portion of the PPG waveform, and/or determining a root sum of squares (RSS) from the dynamic portion of the PPG waveform. The emitted light may be transmitted through tissue of the human subject. The method may include detecting the transmitted light and outputting the representation of a photoplethysmography (PPG) waveform for each of the one or more wavelengths. The emitted light may be scattered in tissue of the human subject. The method may include detecting reflected scattered light at outputting the representation of a photoplethysmography (PPG) waveform for each of the one or more wavelengths.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 7 shows an example of the measure of the amplitude of the representation of the photoplethysmography (PPG) waveform output by the processing subsystem shown in FIGS. 1A and 1B in response to the detected light from emitter E-12 by the detector;

FIG. 8 shows an example of the measure of the amplitude of the representation of the PPG waveform output by the processing subsystem shown in FIGS. 1A and 1B in response to the detected light from emitter E-14 by the detector;

FIG. 9 shows an example of the measure of the amplitude of the representation of the PPG waveform output by the processing subsystem shown in FIGS. 1A and 1B in response to the detected light from emitter E-16 by the detector, FIG. 10 shows an example of the measure of the amplitude of the representation of the PPG waveform output by the processing subsystem shown in FIGS. 1A and 1B in response to the detected light from emitter E-18 by the detector.

DETAILED DESCRIPTION OF THE INVENTION

Figure 1A:
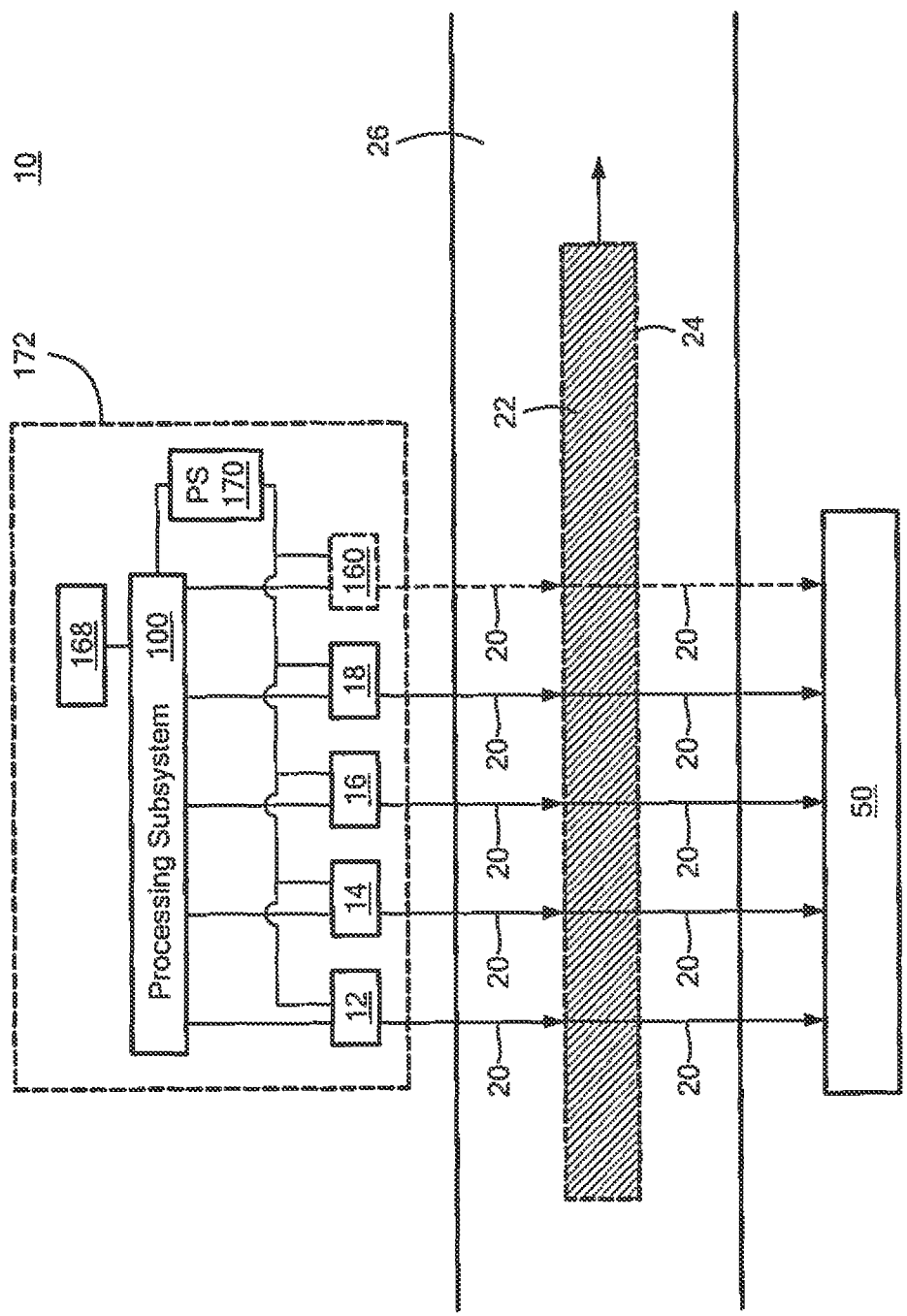
FIG. 1A is a schematic block diagram showing the primary components of one example of the system for noninvasively measuring blood alcohol concentration in blood using light.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1B:
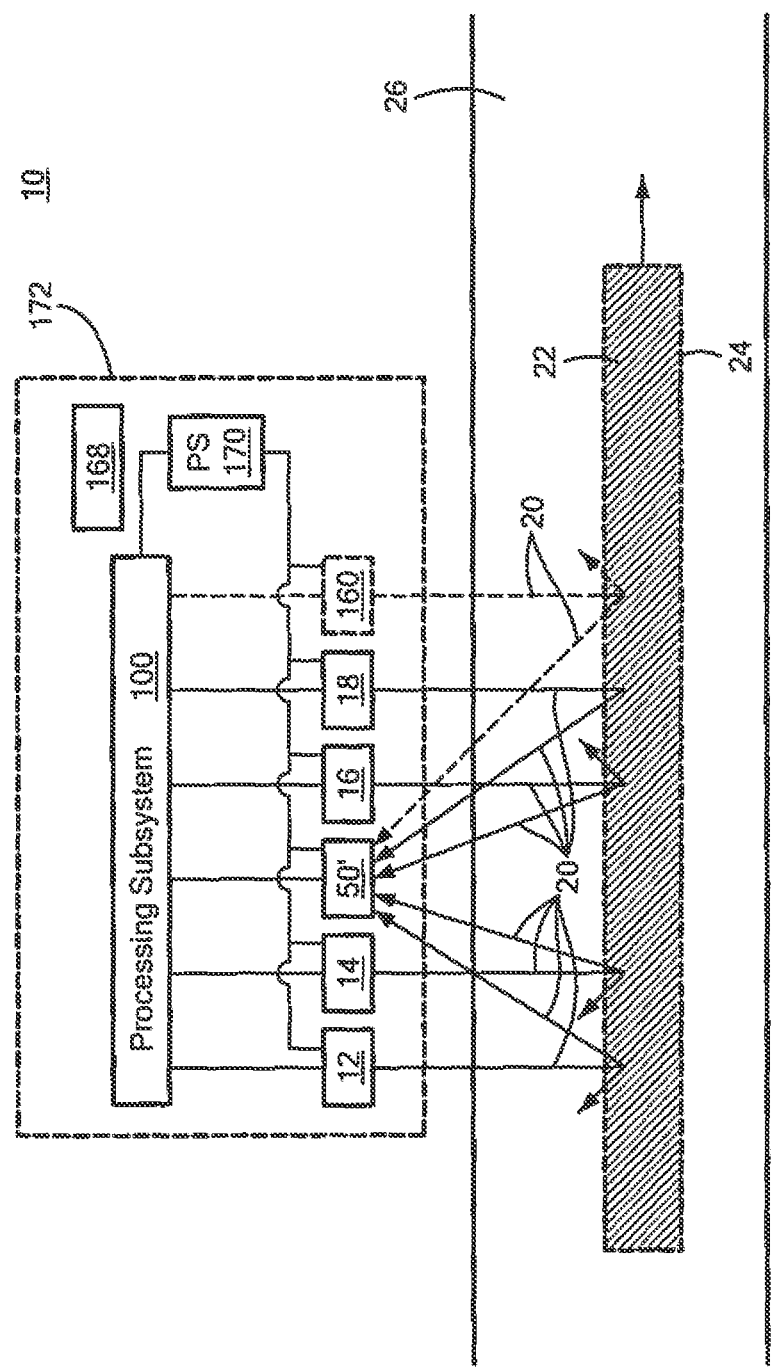
FIG. 1B is a schematic block diagram showing the primary components of another example of the system for noninvasively measuring blood alcohol concentration in blood using light.

System 10, FIGS. 1A and 1B, for noninvasively measuring blood alcohol concentration in blood using light includes one or more emitters, e.g., emitters 12, 14, 16 and 18, each configured to emit light 20 in the near infrared light spectrum (e.g., about 1,250 nm to about 2,500) or the infrared light spectrum (e.g., about 2,500 nm to about 50,000 nm) at one or more wavelengths that respond to varied chromophore concentrations of alcohol, e.g., ethanol, and water in the blood 22 of artery or vein 24 of a human subject. In the example shown in FIG. 1A, light 20 at the one or more wavelengths provided by one or more of emitters 12, 14, 16, and 18 is shown transmitting through tissue 26, e.g., the tissue of an area of the human subject, such as an arm, wrist, leg, foot, ankle, hand, finger, and the like, through blood 22 and exiting tissue 26 as shown. In the example shown in FIG. 1B, light 20 at the one or more wavelengths provided by one or more of emitters 12, 14, 16, and 18 is shown scattering through tissue 26 and then reflecting from blood 22 as shown. Although as shown in FIGS. 1A and 1B, system 10 includes four emitters 12, 14, 16, and 18, system 10 may include only one emitter or may include more than four emitters, as needed and known by those skilled in the art.

Each of emitters 12, 14, 16, and 18 is preferably a small sized, compact emitter, e.g., having a size of about 9 mm in diameter, e.g., available from Eblana Photonics, Dublin, Ireland, Model No. EP1278-DM-TP39. One or more of emitters 12, 14, 16, and 18 are preferably configured to emit light 20 at one or more wavelengths using narrow wavelength light emitting diodes (LEDs), laser diodes, or similar small sized, compact narrowband light sources that can be integrated into a wearable device, e.g., the size of wearable fitness device, a smartwatch, and the like, as discussed below.

One or more of emitters 12, 14, 16, and 18 preferably emit light 20 at the one or more wavelengths of light that respond to varied chromophore concentrations in blood 22 of the human subject, e.g., ethanol, water, oxygenated blood, glucose, and the like. In one design, the one or more wavelengths of light 20 emitted by emitters 12, 14, 16, and 18 may be determined or selected by an absorptivity or scattered reflectance light spectrum of alcohol and/or an absorptivity or scattered reflectance light spectrum of water. For example, emitter 12 may be configured to emit light 20 at one or more wavelengths preferably having a wavelength of about 1700 nm, indicated at 24, FIG. 2, associated with peak 26 of absorptivity or scattered reflectance light spectrum plot 22 of ethanol, emitter 14 may be configured to emit light 20 at one or more wavelengths having a wavelength of about 1900 nm, indicated at 28, associated with peak 30 of absorptivity or scattered reflectance light spectrum plot 32 of water, emitter 16 may be configured to emit light 20 at one or more wavelengths having a wavelength of about 2100 nm, indicated at 34, associated with peak 36 of light absorptivity or scattered reflectance plot 22 of ethanol, and emitter 18 may be configured to emit light 20 at one or more wavelengths having a wavelength of about 2300 nm, indicated at 38, associated with peak 40 of absorptivity or scattered reflectance light spectrum plot 22 of ethanol.

Figure 3:
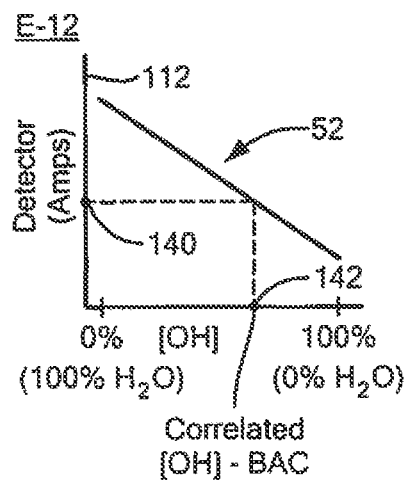
FIG. 3 is a plot showing one example of a molar alcohol absorptivity plot referenced by the measured amplitude for the one or more wavelengths provided by emitter E-12 shown in FIG. 1A and FIG. 1B.
Figure 4:
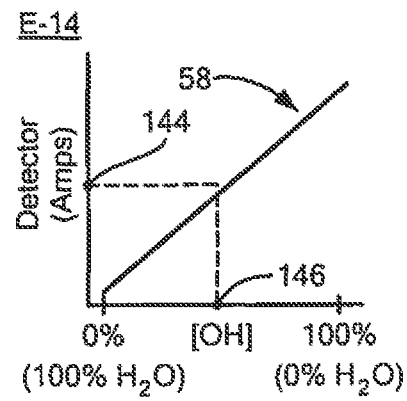
FIG. 4 is a plot showing one example of a molar alcohol absorptivity plot referenced by the measured amplitude for the one or more wavelengths provided by emitter E-14 shown in FIG. 1A and FIG. 1B.
Figure 5:
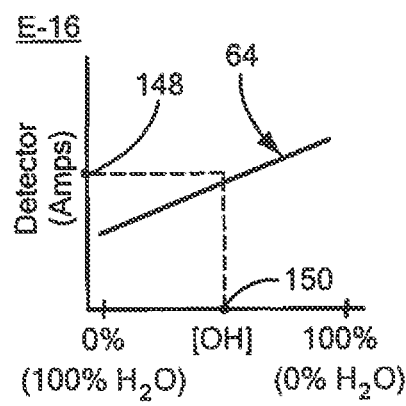
FIG. 5 is a plot showing one example of a molar alcohol absorptivity plot referenced by the measured amplitude for the one or more wavelengths provided by emitter E-16 shown in FIG. 1A and FIG. 1B.
Figure 6:
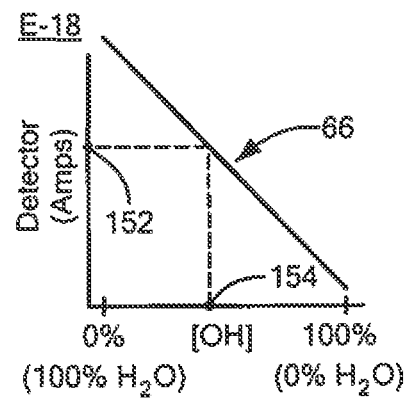
FIG. 6 is a plot showing one example of a molar alcohol absorptivity plot referenced by the measured amplitude for the one or more wavelengths provided by emitter E-18 shown in FIG. 1A and FIG. 1B.

The one or more wavelengths of light 20 emitted by one or more of emitters 12, 14, 16, and 18 may also be determined or selected by referencing one or more molar absorptivity plots. A molar absorptivity plot preferably spans the full light spectrum of near infrared or infrared light and provides the molar reflectance/absorptivity, a linear slope of concentration/molarity versus absorbance/reflectance for each of the one or more wavelengths, and may be used to select or determine the one or more wavelengths with the highest slope (response to change in concentration). For example, FIG. 3 shows an example of a molar absorptivity plot 52 for emitter 12, FIGS. 1A and 1B, which emits light 20 at one or more wavelengths having a wavelength of about 1700 nm for peak 26, FIG. 2, where the absorption or scattering at alcohol and water solutions ranging between a solution of 100% alcohol and a solution of 100% water is measured. FIG. 4 shows an example of molar absorptivity plot 58 for emitter 14 which emits light at one or more wavelengths having a wavelength of about 1900 nm for peak 30 where the absorption or scattering at alcohol and water solutions ranging between a solution of 100% alcohol and a solution of 100% water is measured. FIG. 5 shows an example of molar absorptivity plot 64 for emitter 16 which emits light at one or more wavelengths having a wavelength of about 2100 nm for peak 36 where the absorption or scattering at alcohol and water solutions ranging between a solution of 100% alcohol and a solution of 100% water is measured. FIG. 6 shows an example of molar absorptivity plot 66 for emitter 18 which emits light at one or more wavelengths having a wavelength of about 2300 nm for peak 40 where the absorption or scattering at alcohol and water solutions ranging between a solution of 100% alcohol and a solution of 100% water is measured.

As known by those skilled in art, the slopes shown in FIGS. 3-6 are dependent on if water or alcohol absorbs more transmitted light when compared to each other. For example, if water absorbs more light than alcohol, as the alcohol concentration is increased, more light will be transmitted through to the detector and the response of the light by the detector will go up. This example would constitute a positive slope, e.g., as shown in FIGS. 4 and 5 for emitters E-14 and E-16. If alcohol absorbs more light than water, the opposite would be true and a negative slope would be the result, e.g., as shown in FIGS. 3 and 6 for emitters E-12 and E-18. In terms of scattering, if alcohol scatters more light than water, higher concentrations would scatter light back to the detector constituting a higher response for increased alcohol concentrations and a positive slope. The opposite is true (negative slope) if water scatters more light than alcohol.

System 10, FIGS. 1A and 1B, also includes one or more detectors, e.g., detector 50, FIG. 1A, or detector 50' FIG. 1B, which detect light 20 emitted at the one or more wavelengths emitted by one or more of emitters 12, 14, 16, and 18 discussed above, e.g., transmitted light 20 as shown in FIG. 1A or reflected scattered light 20 as shown in FIG. 1b. Detector 50, 50' outputs a representation of a PPG waveform in response to detected one or more of the one or more wavelengths emitted by emitters 12, 14, 16, and 18 discussed above. For example, FIG. 7 shows an example of the representation of PPG waveform 68 for the one or more wavelengths output by detector 50, 50', FIGS. 1A and 1B, in response td light 20 detected by detector 50, 50' from emitter 12. PPG waveform 68 preferably includes static portion 70 and dynamic portion 72. As known by those skilled in the art, the static portion of a PPG waveform varies with all characteristics of each human subject, the activities of each human subject, and the environment where the human subject is located and dynamic portion varies with each blood volume change associated with the heartbeat of the human subject. In this example, detector 50, 50', FIGS. 1A and 1B, also preferably outputs a PPG waveform 74, FIG. 8, in response to the light 20 detected from emitter 14 with static portion 76 and dynamic portion 78. Detector 50, 50' also preferably outputs PPG waveform 80, FIG. 9, in response to the light 20 detected from emitter 16 with static portion 82 and dynamic portion 84 of PPG waveform 86, FIG. 10, in response to the light 20 detected from emitter 18.

One advantage of using the dynamic portion of the PPG waveform by system 10 and the method thereof, discussed below, is that common factors that impact spectroscopy, such as tissue density, hydration, melanin concentration, ambient light, and the like, e.g., in static portions 70, 76, 82, and 88, FIGS. 7-10, of PPG waveforms 68, 74, 80, and 86, respectively, are calculated out by processing subsystem 100 which preferably uses the quiescent portion of the cardiac cycle to remove the absorbance due to static tissue and fluid, e.g., the dynamic portions 72, 78, 84, and 90 of the PPG waveforms 68, 74, 80, and 86, respectively.

Detector 50, 50', FIGS. 1A and 1B, is preferably a small sized, compact detector, having a size of less than about 5 cm by about 5 cm, e.g., available from Thorlabs, Newton, N.J., Model No. FDPS3X3, such that system 10 can be configured as a wearable device, as discussed below.

System 10 also includes processing subsystem 100, FIGS. 1A and 1B, coupled to one or more emitters 12, 14, 16, and 18 and one or more detectors 50 as shown. Processing subsystem 100 determines a measure of an amplitude of the representation of the PPG waveform for each of the one or more wavelengths and determines the blood alcohol concentration (BAC) by referencing the measured amplitude for each of the one or more wavelengths to a molar absorptivity plot which indicates a measure of the absorptions or scattering at alcohol and water solutions ranging between a solution of 100% alcohol and a solution of 100% water.

For example, in one design, processing subsystem 100 preferably determines a measure of the amplitude of the representation of the PPG waveform for each of the one or more wavelengths by one or more of: determining a difference between a maximum PPG value and a minimum PPG value from the dynamic portion of the PPG waveform, determining a route mean square (RMS) value from the dynamic portion of the PPG waveform, determining a maximum PPG peak value from the dynamic portion of the PPG waveform, determining a minimum PPG peak value from the dynamic portion of the PPG waveform, and/or determining a root sum of squares (RSS) from the dynamic portion of the PPG waveform.

In this example, processing subsystem 100 preferably determines a measure of one or more of amplitudes 102, 104, 106, or 108, FIG. 7, of the representation of the PPG waveform associated with emitter 12 by determining a difference between a maximum PPG value and a minimum PPG value from any of amplitudes 102, 104, 106, or 108 from dynamic portion 72 of the PPG waveform 68, where the maximum PPG value is exemplarily indicated at 130 and minimum PPG value is indicated at 132. Processing subsystem 100 may also determine a measure of one or more of amplitudes 102, 104, 106, or 108 of the representation of the PPG waveform 68 associated with emitter 12 by determining a RMS value from dynamic portion 72 of the PPG waveform 68 or determining a RSS value from dynamic portion 72 of the PPG waveform 68. Processing subsystem 100 may also determine the measure of one or more of amplitudes 102, 104, 106, or 108 of the representation of the PPG waveform 68 associated with emitter 12 by determining a maximum PPG value of dynamic portion 72 of PPF waveform 68, exemplarily indicated at 130 or determining a minimum PPG value of dynamic portion 72 of PPF waveform 68, exemplarily indicated at 130.

In a similar manner, processing subsystem 100 preferably determines a measure of one or more of amplitudes 110, 112, or 114, FIG. 8, of PPG waveform 74, associated with emitter 14, amplitudes 116, 118, or 120, FIG. 9, of the representation of PPG waveform 80 associated with emitter 16, or amplitudes 122, 124 or 126, FIG. 10, of the representation of PPG waveform 86 associated with emitter 18.

Processing subsystem 100 determines the BAC by referencing the measured amplitude for each of the one or more wavelengths discussed above to a molar absorptivity plot which indicates a measure of the absorptions or scattering at alcohol and water solutions ranging between a solution of 100% alcohol and a solution of 100% water.

For example, the determined value of the measure of one or more of amplitudes 102, 104, 106, or 108, FIG. 7, of the representation of the PPG waveform 68 associated with emitter 12 provided by processing subsystem 100 is referenced to a molar absorptivity plot which indicates a measure of the absorptions or scattering at alcohol and water solutions ranging between a solution of 100% alcohol and a solution of 100% water, e.g., the determined value indicated at point 140, FIG. 3, of the measure of one or more of amplitudes 102, 104, 106, or 108 is referenced to molar alcohol absorptivity plot 52 for emitter 12, and the level of alcohol, e.g., ethanol, in the blood 22, FIGS. 1A and 1B, is determined, indicated at 142, which correlates to BAC.

The same process is preferably performed by processing subsystem 100 using the determined the value of the measure of one or more of amplitudes 110, 112, or 114, FIG. 8 of PPG waveform 74, e.g., the determined value indicated a point 144, FIG. 4, referenced to molar absorptivity plot 58 for emitter 14 to determine BAC, indicated at 146, the determined the value of the measure of one or more of amplitudes 116, 118, or 120, FIG. 9, of PPG waveform 80, e.g., the determined value indicated a point 148, referenced to molar absorptivity plot 64 for emitter 16 to determine BAC, indicated at 150, and/or determine the determined value of the measure of one or more of amplitudes 122, 124 or 126, FIG. 10, of PPG waveform 86, e.g., the determined value indicated a point 152, FIG. 6, which is referenced to molar absorptivity plot 66 for emitter 18 to determine BAC, indicated at 154.

Processing subsystem 100, FIGS. 1A and 1B, is preferably configured to average the determined BAC at each of the one or more wavelengths to enhance the accuracy of the measured blood alcohol concentration.

In one design, processing subsystem 100 may rapidly and sequentially turn on and off one of more of emitters 12, 14, 16, and 18 emitting light 20 at the one or more wavelengths. In another design, processing subsystem 100 may continuously turn on one or more of emitters 12, 14, 16, and 18 such that light 20 is continuously emitted.

Processing subsystem 100 may be a processor, one or more processors, an application-specific integrated circuit (ASIC), firmware, hardware, digital circuitry, analog circuitry, a combination of digital circuitry and analog circuitry, and/or software (including firmware, resident software, micro-code, and the like) or a combination of both hardware and software. Processing subsystem 100 also preferably includes one or more programs stored in a memory which are preferably configured to be executed by the one or more processors. Computer program code for the programs for carrying out the instructions or operation of processing subsystem 100 may be written in any combination of one or more programming languages, including an object-oriented programming language, e.g., C++, Smalltalk, Java, and the like, or conventional procedural programming languages, such as the "C" programming language, Assembly language or similar programming languages.

Processing subsystem 100 and/or detector 50, 50' may provide the representation of the PPG waveform for each of the one or more wavelengths discussed above with reference to one or FIGS. 7-10 as an analog representation or a digital representation, as known by those skilled in the art.

Figure 2:
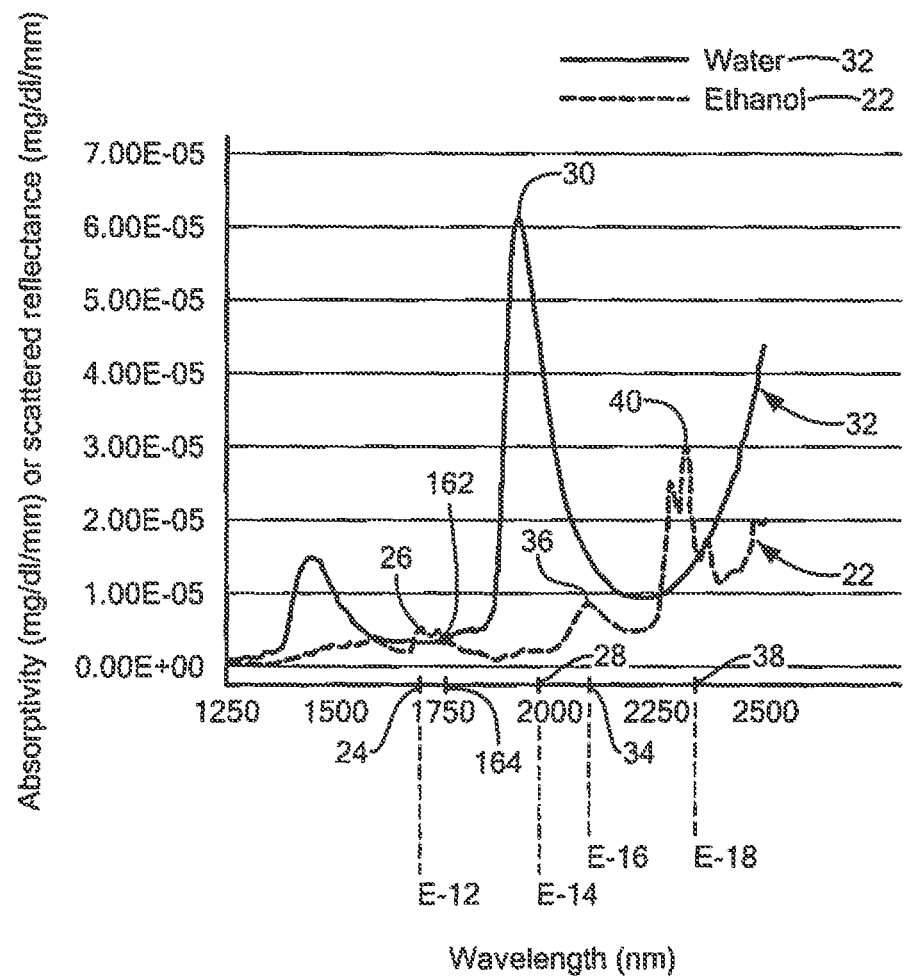
FIG. 2 depicts plots showing examples of an absorptive light spectrum of alcohol and an absorptivity light spectrum of water.
Figure 11:
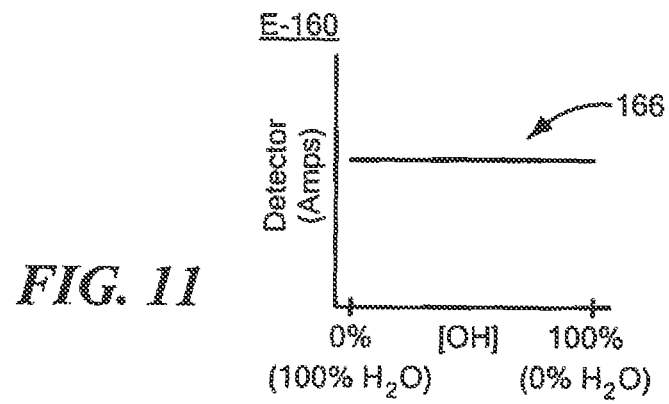
FIG. 11 shows an example of a molar alcohol absorptivity plot where a difference between absorptions or scattering between a solution of 100% alcohol and a solution of water is measured when the ratio of alcohol concentration and water concentration are the same.

In one design, system 10, FIGS. 1A and 1B, also preferably includes emitter 160 coupled to processing subsystem 100 which is preferably emits light at the one or more wavelengths having a wavelength where absorptivity or scattered reflectance light spectrum 32 of water, FIG. 2, and absorptivity or scattered reflectance light spectrum 22 of alcohol intersect, e.g., at point 162 at about 1800 nm, indicated 164, or any of the points where absorptivity or scattered reflectance light spectrum 32 of water and scattered reflectance absorptivity or scattered reflectance light spectrum 22 of alcohol intersect. When emitter 160, FIG. 1, emits light at this wavelength, the ratio of the alcohol concentration and the water concentration are the same and molar absorptivity plot 166, FIG. 11, will be zero, e.g., a flat line as shown. Processing subsystem 100 is preferably configured to reference one or more of the one or more wavelengths emitted by one or more of emitters 12, 14, 16, and 18 discussed above to a wavelength with a molar absorptivity plot of zero to further increase the accuracy of the BAC detected. This allows system 10 and the method thereof to continuously calibrate itself by allowing this reference to increase and decrease with certain hemodynamic changes, but its increase and decrease will not be due to alcohol. Thus, as a reference, it can eliminate other factors that may be impacting the estimating of BAC.

Figure 12:
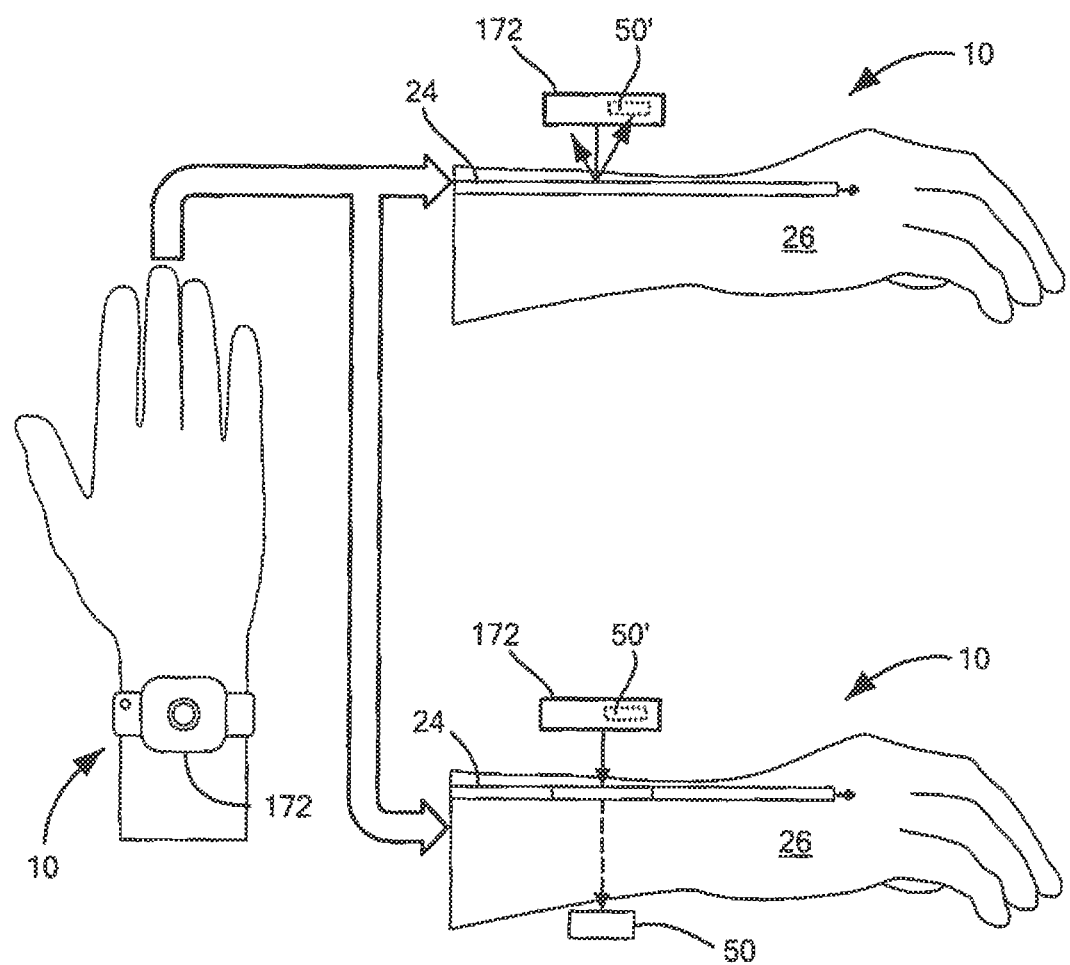
FIG. 12 shows one example of the system and method for noninvasively measuring blood alcohol concentration using light shown in one or more of FIGS. 1-11 configured as a wearable device.

System 10, FIGS. 1A and 1B, preferably include memory 168 coupled to processing subsystem and power supply 170 coupled to processing subsystem 100, one or more of emitters 12, 14, 16, and 18, and detector 50, 50' as shown. Memory 168 and power supply 190 preferably each have a small compact size. As discussed above, one or more of emitters 12, 14, 16, 18, detector 50, 50' and processing subsystem 100 also have a small, compact size. In one design, one or more of emitters 12, 14, 16, 18, detector 50, 50', processing subsystem 100, memory 168, and power supply 170 are enclosed in small compact housing 172 such that system 10 may be configured as a wearable device, e.g., the size of a Fitbit®, smartwatch, or similar type device, e.g., as shown in FIG. 12.

As discussed above with reference to one or more of FIGS. 1-12, system 10 may rely on the transmission of light 20, FIG. 1A, at the one or more wavelengths provided by one or more of one or emitters 12, 14, 16, and 18 through tissue 26 and blood 22 of a human subject. In this example, one or more detectors 50 are preferably located on an opposite side of tissue 26 as one or more emitters 12, 14, 16, and 18 as shown and detect light 20 at one or more wavelengths transmitted though tissue 26 including blood 22 in artery or vein 24. System 10 may also rely on the scattering of light 20, FIG. 1B, at the one or more wavelengths provided one or more of emitters 12, 14, 16, 18. Scattering of light 20 is related to transmission of light 20 discussed above but instead of detecting light 20 which is transmitted through tissue 24, as shown in FIG. 1A, one or more detectors 50'. FIG. 1B, detect scattered reflected light 20 at one or more wavelengths emitted by one or more one or more emitters 12, 14, 16, and 18 from tissue 26 including blood 22 in artery or vein 24 as shown. In this design, one or more detectors 50' are located on the same side of tissue 26 as one or more of emitters 12, 14, 16, 18 as shown. In this example, the penetration depth of light 20 into tissue 26 may depend on the power applied to one or more emitters 12, 14, 16, and 18 and the separation distance between emitters 12, 14, 16, and 18 and one or more detectors 50'. As known by those skilled in the art, scattering light absorptivity spectrums of alcohol and water may be different from transmission light absorptivity spectrums of alcohol and water as shown in the example shown in FIG. 2, however the same concept still applies to analyzing and determining the concentration of alcohol by system 10 as discussed above.

Figure 13:
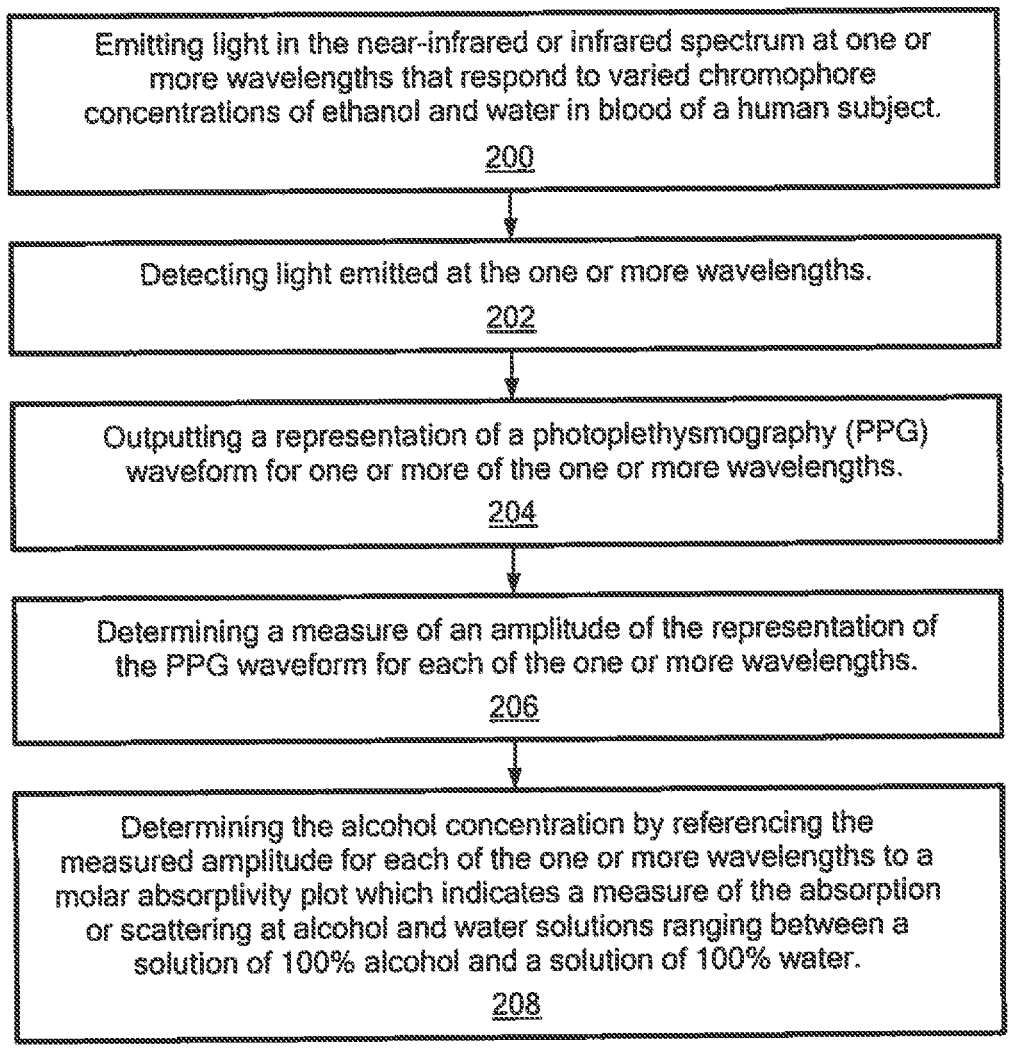
FIG. 13 shows one example of method for noninvasively measuring blood alcohol concentration using light.

One example of the method for noninvasively measuring blood alcohol concentration using light includes emitting light in the near infrared or infrared spectrum at one or more wavelengths that respond to varied chromophore concentrations of ethanol in water in blood of a human subject, step 200. FIG. 13. The method also includes detecting light emitted at the one or more wavelengths, step 202, and outputting a representation of the PPG waveform at each of the one or more wavelengths, step 204. The method also includes determining a measure of an amplitude of the representation of the PPG waveform for each of the one or more wavelengths, step 206, and determining the blood alcohol concentration by referencing the measured amplitude for each of the one or more wavelengths to a molar absorptivity plot which indicates a measure of the absorptions or scattering at alcohol and water solutions ranging between a solution of 100% alcohol and a solution of 100% water, step 208.

The result is system 10 and the method thereof provides a small compact device that can be discretely worn by a user to noninvasively measure blood alcohol concentration in blood using light. System 10 and the method thereof may have a significant impact in both the commercial and medical fields by offering the advantages over conventional system and methods including, inter alia, high accuracy BAC measurements within minutes of alcohol consumption, high temporal resolution to correlate BAC to a physiological and/or psychological response during clinical studies, very small compact size to allow for integration into commercially accepted wearable devices, improved user compliance through discreet measurements, and long hardware lifespan with no moving or consumable components. System 10 and the method thereof also provides users with the ability to passively and accurately monitor their alcohol consumption for personal reasons and also aids the research community to better understand how alcohol consumption correlates to overall health. System 10 and method for noninvasively measuring blood alcohol concentration in blood using light may greatly improve clinician access to high temporally resolute data to broaden their understanding of the short term and long term impacts of alcohol consumption. The information provided by system 10 configured as wearable device may provide users with the ability to monitor their own alcohol consumption with a deeper understanding of the consequences of alcohol consumption.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or them are many other reasons the applicants cannot be expected to describe certain insubstantial substitutes for any claim element amended.

Other embodiments will occur to those skilled in the art and are within the following claims.

What is claimed is:

1. A system for noninvasively measuring blood alcohol concentration using light, the system comprising:
   one or more emitters each configured to emit light in the near infrared or infrared light spectrum at one or more wavelengths that respond to varied chromophore concentrations of ethanol and water in blood of a human subject and configured to emit light at the one or more wavelengths including a wavelength where an absorptivity or scattered reflectance light spectrum of water and an absorptivity or scattered reflectance light spectrum of alcohol intersect;
   one or more detectors configured to detect the light emitted at the one or more wavelengths and output a representation of a photoplethysmography (PPG) waveform for one or more of the one or more wavelengths; and
   a processing subsystem coupled to the one or more emitters and the one or more detectors, the processing subsystem further configured to rapidly and sequentially turn on and turn off one or more of the one or more emitters emitting light at the one or more wavelengths, the processing subsystem further configured to determine a measure of an amplitude of the representation of the PPG waveform for each of the one or more wavelengths and determine the blood alcohol concentration by referencing the measured amplitude for each of the one or more wavelengths to a molar absorptivity plot, the processing subsystem further configured to reference one or more of the one or more wavelengths emitted by one or more of emitters to a wavelength where a ratio of the alcohol concentration and the water concentration are the same to further increase the accuracy of the determined blood alcohol concentration.

2. The system of claim 1 wherein the processing subsystem is further configured to average the determined blood alcohol concentration at each of the one or more wavelengths to enhance the accuracy of the measured blood alcohol concentration.

3. The system of claim 1 in which the light emitted by the one or more emitters at the one or more wavelengths is determined by one or more of: an absorptivity or scattered reflectance light spectrum of water, an absorptivity or scattered reflectance light spectrum of alcohol, and/or the molar alcohol absorptivity plot.

4. The system of claim 3 in which the one or more detectors are configured to detect light emitted at one or more wavelengths determined by the one or more of: the absorptivity or scattered reflectance light spectrum of water, the absorptivity or scattered reflectance light spectrum of alcohol, and/or the molar alcohol absorptivity plot.

5. The system of claim 1 in which the one or more detectors are configured to provide the representation of the PPG waveform for each of the one or more wavelengths as an analog representation.

6. The system of claim 1 in which the one or more detectors are configured to provide the representation of the PPG waveform for each of the one or more wavelengths as a digital representation.

7. The system of claim 1 in which the processing subsystem is configured to determine the measure of the amplitude of the representation of the PPG waveform for each of the one or more wavelengths by one or more of: determining a difference between a maximum PPG value and a minimum PPG value from a dynamic portion of the PPG waveform, determining a route mean square (RMS) value from the dynamic portion of the PPG waveform, determining a maximum PPG peak value from the dynamic portion of the PPG waveform, determining a minimum PPG peak value from the dynamic portion of the PPG waveform, and/or determining a root sum of squares (RSS) from the dynamic portion of the PPG waveform.

8. The system of claim 7 in which the processing subsystem is configured to determine the blood alcohol concentration by referencing the measured amplitude of the representation of the PPG waveform for each of the one or more wavelengths to a molar absorptivity plot.

9. The system of claim 1 in which the system is configured as a wearable device on the human subject.

10. The system of claim 9 in which one or more of the detectors, the one or more of the emitters, the processing subsystem, a memory, and a power supply each have a small compact size and are enclosed in a wearable housing.

11. The system of claim 1 in which the one or more emitters is configured to emit light which is transmitted through tissue of the human subject.

12. The system of claim 11 in which the one or more detectors are configured to detect the transmitted light at the one or more wavelengths and output the representation of a photoplethysmography (PPG) waveform for one or more of the one or more wavelengths.

13. The system of claim 12 in which at least one of the one or more emitters is located on one side of an area of the human subject and at least one of the one or more detectors is located on an opposite side of the area.

14. The system of claim 1 in which the one or more emitters is configured to emit light which is scattered in tissue of the human subject.

15. The system of claim 14 in which the one or more detectors are configured to detect reflected scattered light at the one or more wavelengths and output the representation of a photoplethysmography (PPG) waveform for one or more of the one or more wavelengths.

16. The system of claim 15 in which at least one of the one of the one or more emitters is located on a same side of an area of the human subject as at least one of the one or more detectors.

17. A method for noninvasively measuring blood alcohol concentration using light, the method comprising:
emitting light in the near-infrared or infrared spectrum at one or more wavelengths that respond to varied chromophore concentrations of ethanol and water in blood of a human subject and emitting light at the one or more wavelengths including a wavelength where an absorptivity or scattered reflectance light spectrum of water and an absorptivity or scattered reflectance light spectrum of alcohol intersect;
detecting light emitted at the one or more wavelengths that respond to varied chromophore concentrations of ethanol and water;
rapidly and sequentially turning on and turning off one or more of the one or more emitters emitting light at the one or more wavelengths;
outputting a representation of a photoplethysmography (PPG) waveform for one or more of the one or more wavelengths;
determining a measure of an amplitude of the representation of the PPG waveform for each of the one or more wavelengths; and
determining the alcohol concentration by referencing the measured amplitude for each of the one or more wavelengths to a molar absorptivity plot in near real time and referencing one or more of the one or more wavelengths to a wavelength where a ratio of the alcohol concentration and the water concentration are the same to further increase the accuracy of the determined blood alcohol concentration.

18. The method of claim 17 further including averaging the determined blood alcohol concentration at each of the one or more wavelengths to enhance accuracy of the measured blood alcohol concentration.

19. The method of claim 17 in which the light emitted at the one or more wavelengths is determined by one or more of: an absorptivity or scattered reflectance light spectrum of water, an absorptivity or scattered reflectance light spectrum of alcohol, and/or the molar alcohol absorptivity plot.

20. The method of claim 19 in which detecting the light includes detecting the light emitted at the one or more wavelengths determined by one or more of: the absorptivity or scattered reflectance light spectrum of water, the absorptivity or scattered reflectance light spectrum of alcohol, and/or the molar alcohol absorptivity plot.

21. The method of claim 17 in which the representation of the PPG waveform for each of the one or more wavelengths is an analog representation.

22. The method of claim 17 in which the representation of the PPG waveform for each of the one or more waveforms is a digital representation.

23. The method of claim 17 in which determining the measure of the amplitude of the representation of the PPG waveform includes one or more of: determining a difference between a maximum PPG value and minimum PPG value from a dynamic portion of the representation of PPG waveform, determining a route mean square (RMS) value from the dynamic portion of the PPG waveform, determining a maximum PPG peak value from the dynamic portion of the PPG waveform, determining a minimum PPG peak value from the dynamic portion of the PPG waveform, and/or determining a root sum of squares (RSS) from the dynamic portion of the PPG waveform.

24. The method of claim 17 in which the emitted light is transmitted through tissue of the human subject.

25. The method of claim 24 further including detecting the transmitted light and outputting the representation of a photoplethysmography (PPG) waveform for each of the one or more wavelengths.

26. The method of claim 17 in which the emitted light is scattered in tissue of the human subject.

27. The method of claim 26 further including detecting reflected scattered light at outputting the representation of a photoplethysmography (PPG) waveform for each of the one or more wavelengths.

* * * * *